United States Patent [19]
Theuer

[11] Patent Number: 5,892,149
[45] Date of Patent: Apr. 6, 1999

[54] HEAT TRANSFER MONITORING AND/OR MEASURING DEVICE

[75] Inventor: Thomas Theuer, Tettnang, Germany

[73] Assignee: i f m electronic GmbH, Essen, Germany

[21] Appl. No.: 863,945

[22] Filed: May 27, 1997

[30] Foreign Application Priority Data

May 24, 1996 [DE] Germany .................. 196 21 173.5

[51] Int. Cl.⁶ .................................................. G01F 1/68
[52] U.S. Cl. ............................................. 73/204.22
[58] Field of Search .............. 73/204.22, 204.26; 439/465, 467, 731

[56] References Cited

U.S. PATENT DOCUMENTS

| | | | |
|---|---|---|---|
| 4,639,054 | 1/1987 | Kersbergen | 439/465 |
| 4,648,270 | 3/1987 | Johnson et al. | 73/204.22 |
| 4,728,296 | 3/1988 | Stamm | 439/465 |
| 4,776,214 | 10/1988 | Moran et al. . | |
| 4,815,280 | 3/1989 | Tujimura et al. | 73/204.22 |
| 4,829,818 | 5/1989 | Bohrer | 73/204.22 |
| 5,337,604 | 8/1994 | Van Bavel et al. | 73/204.22 |
| 5,741,968 | 4/1998 | Arai | 73/204.22 |

FOREIGN PATENT DOCUMENTS

| | | |
|---|---|---|
| 24 47 617 | 4/1976 | Germany . |
| 26 29 051 | 1/1978 | Germany . |
| 29 18 433 | 12/1980 | Germany . |
| 32 13 902 | 10/1983 | Germany . |
| 38 11 728 | 9/1988 | Germany . |
| 37 13 981 | 11/1988 | Germany . |
| 38 25 059 | 8/1989 | Germany . |
| 39 11 008 | 5/1990 | Germany . |
| 38 44 354 | 7/1990 | Germany . |
| 39 43 437 | 10/1990 | Germany . |

*Primary Examiner*—Richard Chilcot
*Assistant Examiner*—Jewel V. Thompson
*Attorney, Agent, or Firm*—Sixbey, Friedman, Leedom & Ferguson; David S. Safran

[57] ABSTRACT

A heat transfer indicating device for monitoring and/or measuring a flowing medium, especially a flow indicator and/or a flowmeter, with a preferably flexible component carrier (1), with electrical and/or electronic components (2) on the component carrier (1) and connected to one another to form a circuit, with a heating element (3), with temperature measuring element (4), with electrical connection (5) and with a housing. The flow indicator can be produced with relatively low cost, is relatively simple to mount, and can be easily re-opened again so that it can be repaired in case of a defect and the parts not affected by the defect can be re-used, by the fact that component carrier (1) is formed of two component carrier halves (1a, 1b) located on top of one another and between which the heating element (3) and temperature measuring element (4) are located.

17 Claims, 9 Drawing Sheets

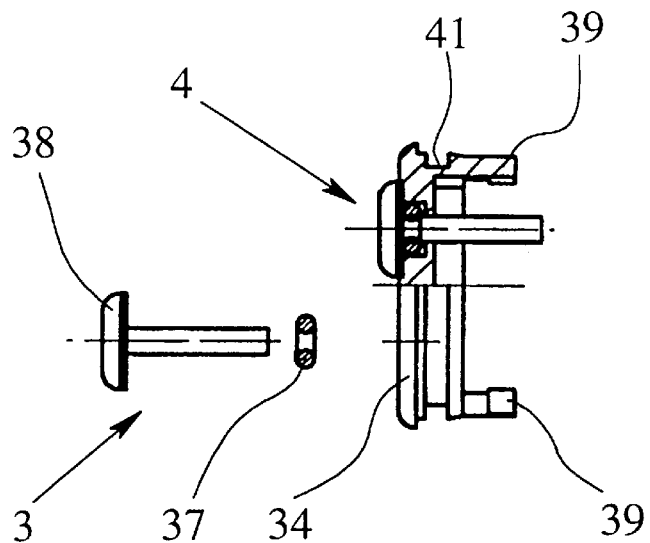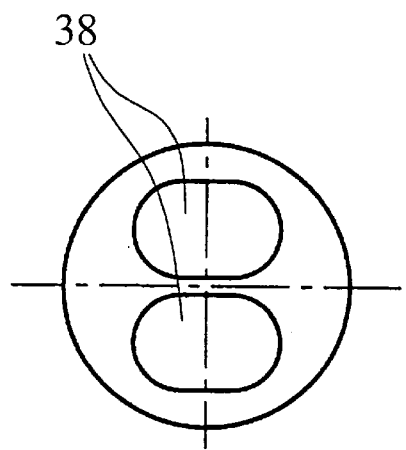
Fig. 13  Fig. 14
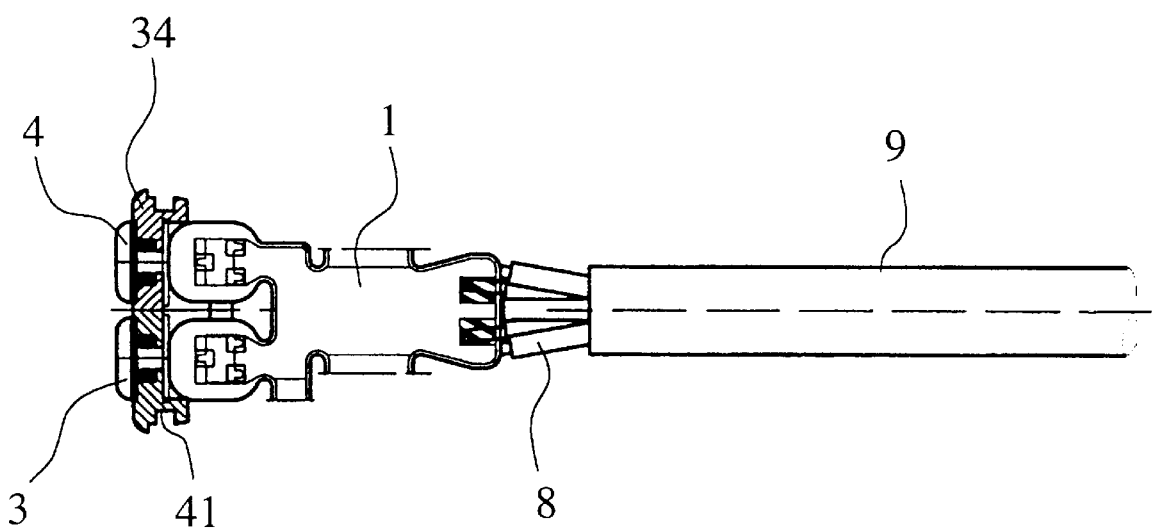
Fig. 15

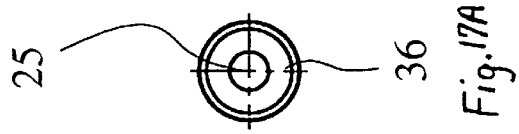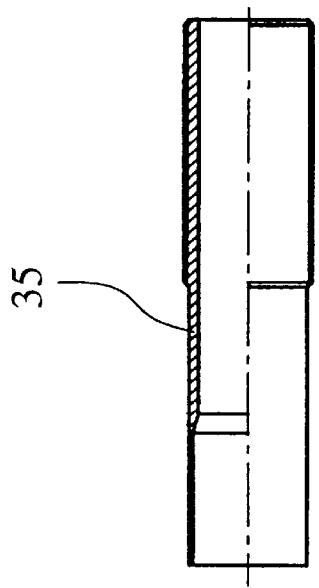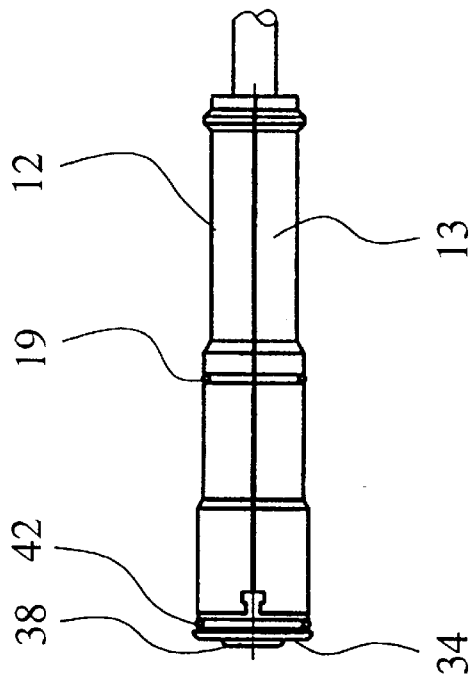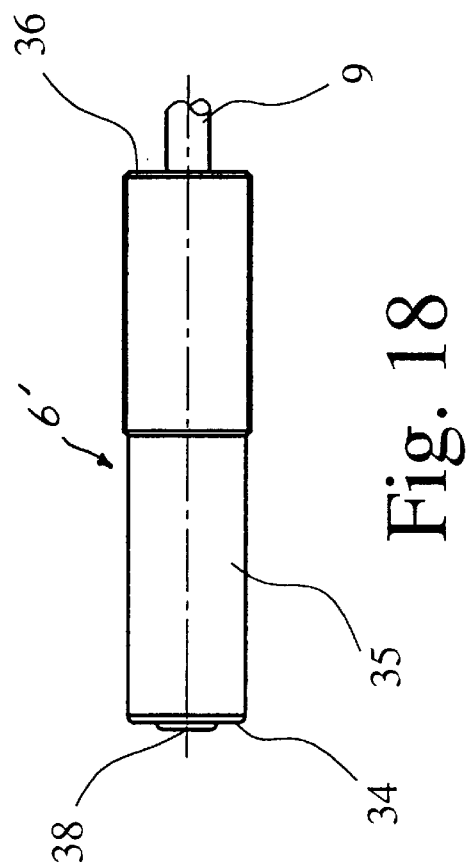

HEAT TRANSFER MONITORING AND/OR MEASURING DEVICE

BACKGROUND OF THE INVENTION

1. Field of the Invention

The invention relates to a heat transfer monitoring and/or measuring device, especially a flow indicator and/or a flowmeter for flowing media, with a preferably flexible component carrier, preferably with electrical and/or electronic components, with a heating element, with at least one temperature measuring element, with an electrical connection possibility and with a housing. In particular, to such a device in which the electrical and/or electronic components are located on the component carrier and are connected to one another to form a circuit and in which the heating element and the temperature measuring element are made pin-shaped.

2. Description of Related Art

It was stated initially that the invention relates to a heat transfer monitoring and/or heat measuring device. Here, heat transfer monitoring device stands for a device in which heat transfer is simply monitored, in which therefore only the presence or absence of a certain heat transfer is ascertained. Conversely, heat transfer measuring device stands for a device in which heat transfer is measured; therefore, an analog measured value which corresponds to the heat transfer is obtained which can also be converted into a digitized measured value. In other words, a heat transfer monitoring device delivers a qualitative statement "heat transfer present" or "heat transfer absent", while a heat transfer measuring device makes a quantitative statement about heat transfer.

Heat transfer monitoring devices or heat transfer measuring devices of the type under discussion here are used especially to record heat transport by flowing media. They are then flow indicators or flowmeters, in the sense of the aforementioned differentiation, a flow indicator corresponding to the heat transfer monitoring device and a flowmeter to a heat transfer measuring device.

Generic heat transfer monitoring devices or heat transfer measuring devices as well as flow indicators or flowmeters work according to the calorimetric principle. Generally, differential temperature measurement is used. A first temperature measuring element measures the actual measured temperature, the measured temperature resulting from the heat output of the heating element, the temperature of the flowing medium and the heat transport capacity of the flow medium which depends on the flow. Furthermore, generally, a second temperature measuring element measures a reference temperature; but, measurement of a reference temperature is not absolutely essential, and can be omitted if, for example, the temperature of the flowing medium is known.

In the prior art heat transfer monitoring and/or measuring devices which operate according to the calorimetric principle, especially flow indicators and/or flowmeters, various embodiments are known (compare German patent document nos 24 47 617; 26 29 051; 32 13 902; 37 13 981; 38 11 728; 38 25 059; 39 11 008; and 39 43 437). In particular, heat transfer monitoring and/or measuring devices of the initially mentioned type are known which have a flexible, more or less film-like component carrier and electrical and/or electronic components, the electrical and/or electronic components being located on the component carrier and being connected to one another to form a circuit.

It is common to all heat transfer monitoring and/or measuring devices of the type to which the invention is directed that:

a) they can only be produced relatively expensively; in particular mounting is expensive;

b) they are generally at least partially potted, therefore at least partially filled with a casting resin;

c) especially due to b), they essentially cannot be opened, and d) due to b) and c), they cannot be repaired in case of a defect and the parts not affected by the defect cannot be re-used.

SUMMARY OF THE INVENTION

A primary object of the invention is to devise a heat transfer monitoring and/or measuring device which can be produced with relatively low cost.

In connection with the foregoing object, it is a further object to devise such a device in which mounting is relatively simple, yet it can also be easily re-opened again, so that it can be repaired in case of a defect and the parts not affected by the defect can be re-used.

According to a first teaching of the invention, the above objects are achieved by the fact that the component carrier is formed of two component carrier halves that are located on top of one another and that the heating element and temperature measuring element are located between the component carrier halves. Preferably, the component carrier is flexible and the two component carrier halves are joined to one another and folded onto one another. The component carrier halves located on top of one another, and optionally folded onto one another, can mechanically fix the heating element and the temperature measuring element. To do this, at least one component carrier half has recesses for partially accommodating the heating element and the temperature measuring element; preferably, both of the component carrier halves are provided with these recesses.

According to a second teaching of the invention, the noted objects are achieved, especially in conjunction with the aforementioned first teaching of the invention, but also independently thereof, by there being two preferably identical half shells which are preferably provided with respective parts a latching means, and the component carrier is located between the half shells and is preferably fixed by the half shells. The heating element and the temperature measuring element each have a peripheral fixing flange and the half shells have recesses which hold the fixing flanges of the heating element and the temperature measuring element. In this way, the heating element and the temperature measuring element, and thus also the component carrier, are fixed in the axial direction with reference to the half shells.

According to a third teaching of the invention, the indicated objects, are achieved, especially in conjunction with one or both of the aforementioned first and second teachings of the invention, but also independently thereof, by the housing being comprised of a lower housing sleeve and an upper housing cover. The housing sleeve can accommodate the component carrier or the half shells which hold the component carrier and which are joined to one another. The upper housing cover, which can be made roughly bell-shaped, first of all, is used as the upper end of the housing sleeve. Otherwise, it is recommended that the necessary electrical connection possibility be accomplished in the area of the housing cover. If a cable set is provided as the electrical connection possibility, preferably, the upper housing cover is provided with a cable penetration. Alternatively, the electrical connection possibility can also be accomplished by an attachment plug which, preferably, is then integrated into the upper housing cover. Finally, it is recommended that the lower housing sleeve, on its side facing the upper housing cover, and the housing cover, on its side facing the housing sleeve, be provided with grooves which run over parts of the periphery and which correspond to one another, so that the housing sleeve and the housing cover can be fixed and joined to one another by a spring washer inserted into the grooves.

According to a fourth teaching of the invention, the underlying object here, especially in conjunction with one or both of the aforementioned first and second teachings of the invention, but also independently thereof, is achieved by the housing being comprised of a lower housing cover, a housing sleeve, and an upper housing cover. Here, the heating element and the temperature measuring element are pushed with an O-ring into the lower housing cover. The housing sleeve can hold the component carrier or the half shells which hold the component carrier and which are joined to one another. The upper housing cover, which is made very flat and preferably elastic, first of all, is used as the upper end of the housing sleeve and can be pressed into it. If a cable set is provided as the electrical connection possibility, preferably the upper housing cover is provided with a cable penetration.

It was also stated at the beginning that the subject of the invention includes a heating element and at least one temperature measuring element. Here, the heating element can also act as the above explained second temperature measuring element; it is then a heating and temperature measuring element.

The component carrier has been designated only as preferably flexible and it is stated that only preferably electrical and/or electronic components are present, therefore, because it is not essential for the teachings of the invention that the component is flexible, it is not essential either for the teachings of the invention whether the heat transfer monitoring and/or measuring device under consideration has electrical and/or electronic components. It is also conceivable that, as the components for which the component carrier is intended, there are only one heating element and one temperature measuring element, while other electrical and/or electronic components which are still necessary overall can be provided in a separated evaluation device.

These and further objects, features and advantages of the present invention will become apparent from the following description when taken in connection with the accompanying drawings which, for purposes of illustration only, show several embodiments in accordance with the present invention.

BRIEF DESCRIPTION OF THE DRAWINGS

FIG. 13 is a side view, partially in section and partially exploded, showing one preferred embodiment of a lower housing cover of the heat transfer monitoring and/or measuring device according to the invention, with a heating element and with a temperature measuring element;

FIG. 14 is a front view of the lower housing cover of FIG. 13;

FIG. 15 shows one embodiment of a component carrier soldered to the heating and temperature measuring elements inserted in the lower housing cover according to FIG. 13, and to the electrical leads of the cable set;

FIG. 17 is a partially exploded, partially sectioned, side view showing the subject according to FIG. 16 in the mounted state and one embodiment of a housing sleeve and an upper housing cover;

FIG. 17A is a front view of the upper housing cover of FIG. 17; and

FIG. 18 shows the subject according to FIG. 17 after the housing sleeve has been pushed over the half shells and the upper housing cover has been pressed into one opening of the housing sleeve.

DETAILED DESCRIPTION OF THE PREFERRED EMBODIMENTS

The invention, as noted above, is a heat transfer monitoring and/or measuring device, especially a flow indicator and/or a flowmeter. In the following, the subject of the invention is always called a heat transfer indicating device for simplicity, but such usage should be considered as encompassing the full range of heat transfer monitoring and/or measuring devices of the types indicated above.

Figure 11:
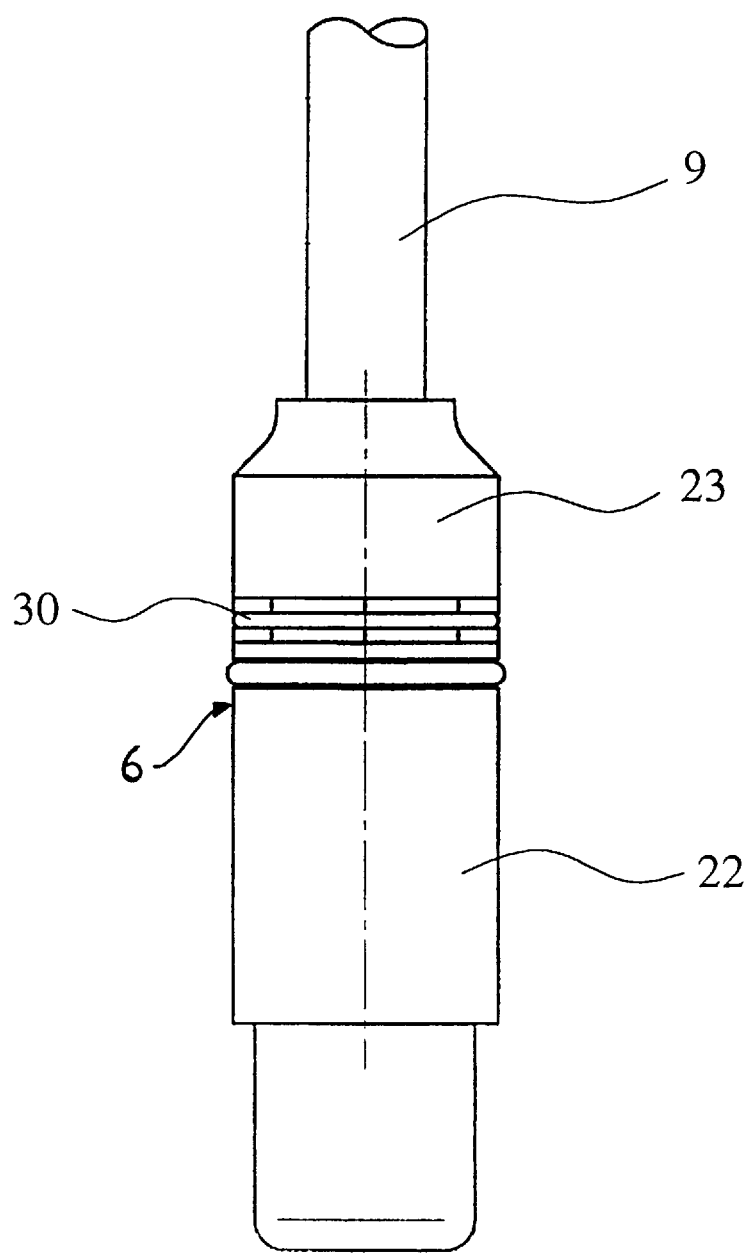
FIG. 11 shows a view of the subject according to FIG. 10 after the lower housing sleeve and the upper housing cover have been joined to one another.

The heat transfer indicating device shown throughout in the figures has, electrical and/or electronic components 2, heating element 3, and a temperature measuring element 4 on a flexible component carrier 1, as well as an electrical connection 5 for the supplying of electrical power to the device, and a housing 6 (FIG. 11). Electrical and/or electronic components 2 on component carrier 1 are connected to one another in a circuit (not shown). Heating element 3 and temperature measuring element 4 are pin-shaped. Examples of such a heating element 3 and temperature measuring element 4 can be found by reference to German patent disclosure document 195 12 111.

In the heat transfer indicating devices shown throughout in the figures, various features are cumulatively embodied which can also be embodied individually.

Figure 1:
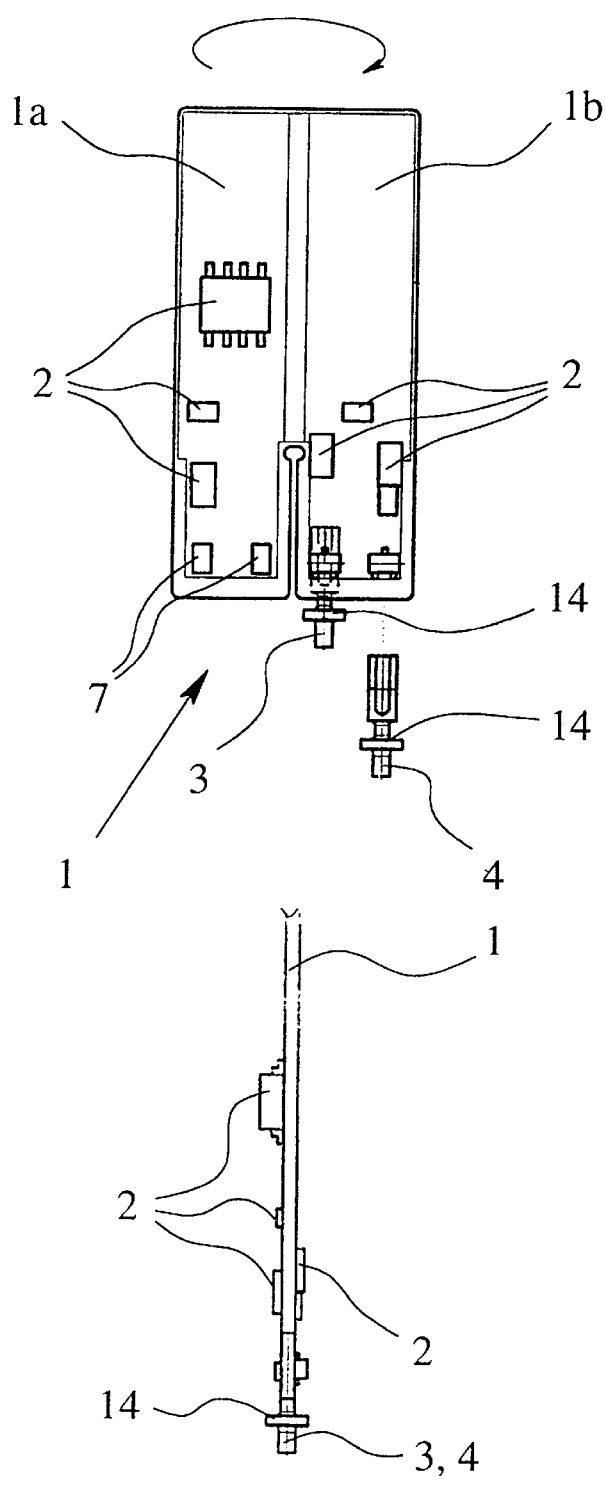
FIG. 1 shows one preferred embodiment of a component carrier of a heat transfer monitoring and/or measuring device according to the invention in the unfolded state together with the heating element and the temperature measuring element belonging to it.
Figure 2:
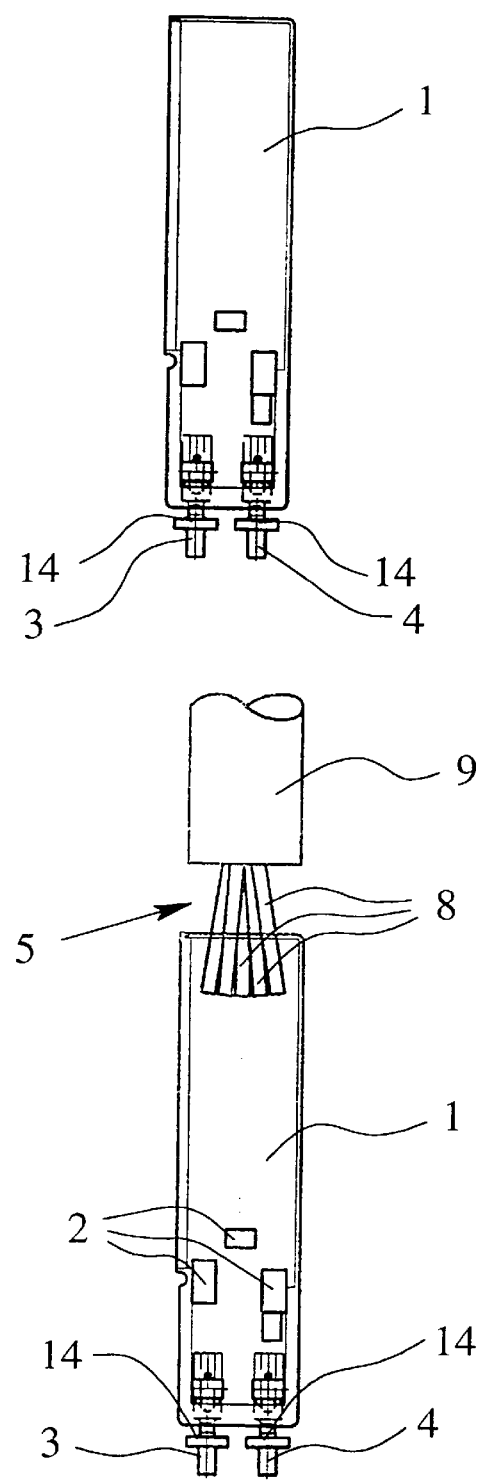
FIG. 2 shows a front view of the embodiment according to FIG. 1, but with the component carrier in the folded state and with the heating element and the temperature measuring element completely mounted.
Figure 3:
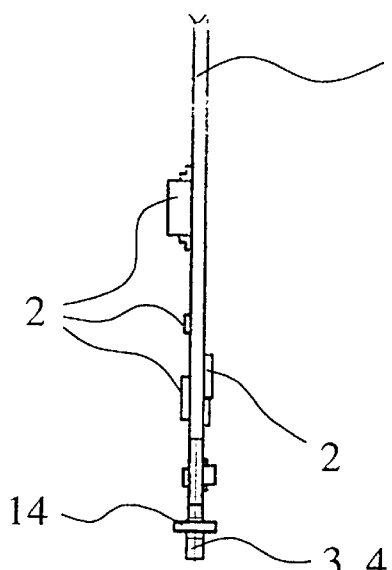
FIG. 3 shows a side view of the subject according to FIG. 2.
Figure 4:
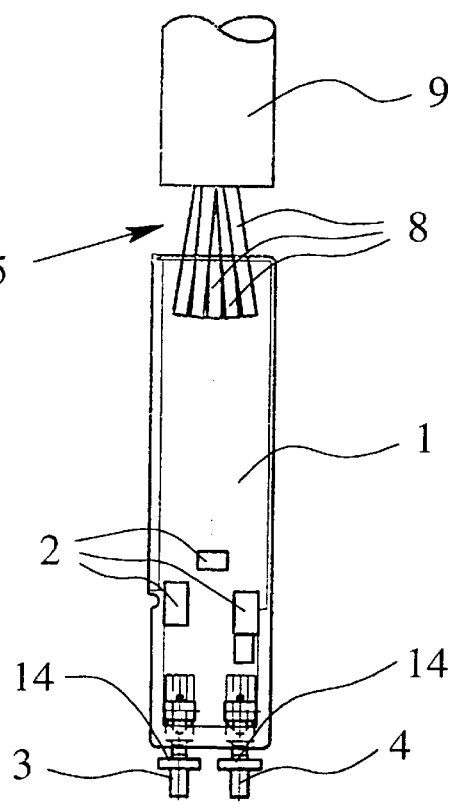
FIG. 4 is a view similar to that FIG. 2 but with a mounted electrical cable set.

First of all, especially FIGS. 1 through 4, show that component carrier 1 comprises two component carrier halves 1a, 1b arranged on top of one another with the heating element 3 and temperature measuring element 4 located between the component carrier halves 1a, 1b. In this embodiment, component carrier 1 is of a flexible film-like construction and the two component carrier halves 1a, 1b are joined to one another. In the assembled state, the two component carrier halves 1a, 1b are folded onto one another, FIG. 1 showing the state of component carrier 1 in which two component carrier halves 1a, 1b have not yet been folded onto one another, while FIGS. 2—4 show component carrier 1 with the component carrier halves 1a, 1b folded onto one another.

Heating element 3 and temperature measurement element 4 are mechanically held by the component carrier halves 1a, 1b being folded onto one another in the illustrated embodiment. FIG. 1 shows the state in which only heating element 3 has been located on component carrier half 1b and the temperature measurement element 4 has not yet been mounted. The component carrier halves 1a, 1b have recesses 7 which are used to partially hold heating element 3 and temperature measuring element 4. Furthermore, the component carrier halves 1a, 1b are provided with electrical printed conductors (not shown) and the heating element 3 and temperature measuring element 4 are soldered to the printed conductors. For the embodiment of the heat transfer indicating device according to the invention shown in FIGS. 1–11, electrical leads 8 of a cable set 9 serve as an electrical connection 5 and are located between component carrier halves 1a, 1b. Electrical leads 8 of the cable set are soldered to printed conductors (not shown) as represented in FIG. 4.

Figure 5:
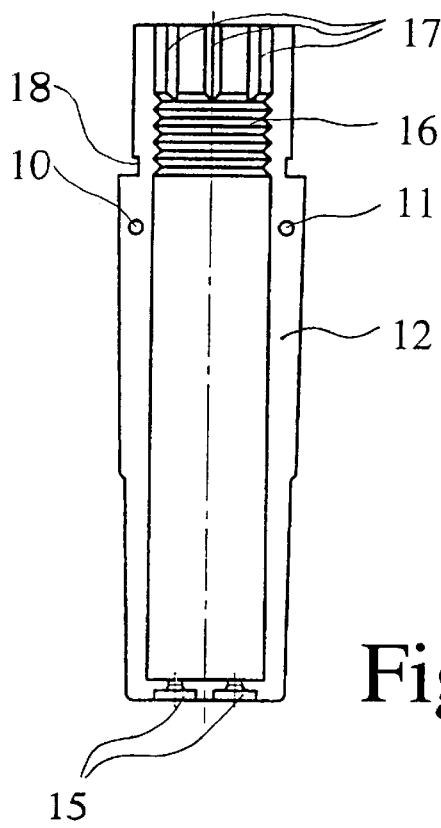
FIG. 5 shows one preferred embodiment of a half shell of the heat transfer monitoring and/or measuring device according to the invention.

As FIGS. 5 though 8 show, in the illustrated embodiment of a heat transfer indicating device according to the invention, two identical half shells 12, 13 are provided which have latching means 10, 11. Component carrier 1 is located between the half shells 12, 13 and is fixed by the half shells 12, 13. The half shells 12, 13 are made of plastic, preferably polyester ether ketone (PEEK) or of polyphenylene sulfide (PPS). Polyester ether ketone is more resistant that polyphenylene sulfide, but is also more expensive. Cheaper polyphenylene sulfide can easily be used for half shells 12, 13.

Figure 6:
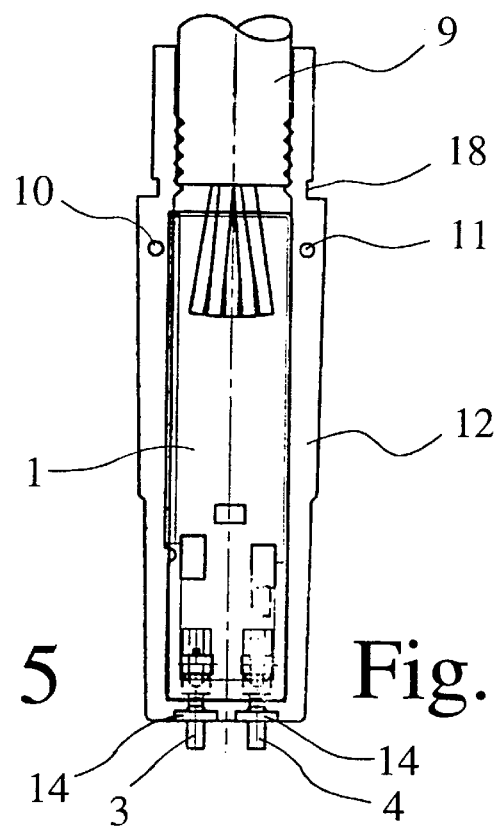
FIG. 6 shows the half shell according to FIG. 5 with the component carrier according to FIG. 4 inserted.

FIG. 5 shows half shell 12, by itself, without component carrier 1 while FIG. 6 shows half shell 12 with component carrier 1 inserted. As FIGS. 1–4 most clearly show, heating element 3 and temperature measuring element 4 each have a peripheral fixing flange 14. The half shells 12, 13 are provided with recesses 15 which hold the fixing flanges 14 of heating element 3 and temperature measuring element 4. In this way, heating element 3 and temperature measuring element 4, and thus, also component carrier 1, are fixed in an axial direction relative to half shells 12, 13.

Figure 7:
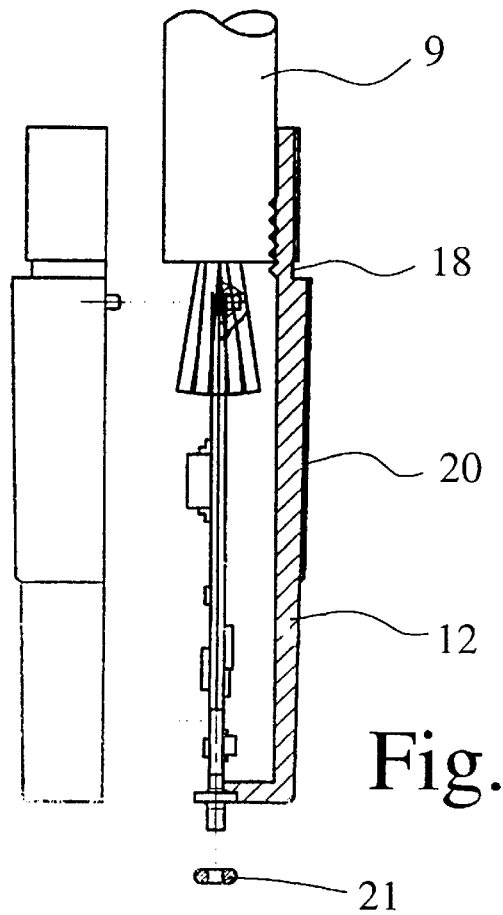
FIG. 7 shows a partially exploded, partial sectioned view, offset 90° relative to the subject according to FIG. 6.

In particular, it can be seen from FIG. 5 that the half shells 12, 13 are provided with ribs 16, 17 which are used for strain relief and locking of cable set 9. Additionally, the half shells 12, 13, as shown in FIGS. 5–7, are provided with a peripheral groove 18 into which an O-ring 19 is inserted (FIG. 8) for holding the half shells 12, 13 together in conjunction with the latching means. Finally, FIG. 7 shows that the half shells 12, 13 are each provided externally with a guide crosspiece 20, the importance of which is explained below.

Figure 8:
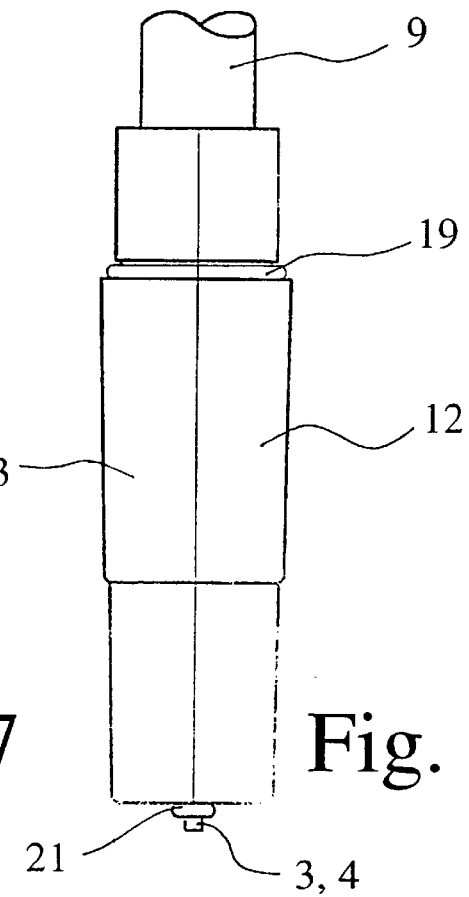
FIG. 8 shows the subject according to FIG. 7 after the two half shells are latched.

FIGS. 7 and 8 show an O-ring 21 which is pushed onto the ends of the heating element 3 and temperature measuring element 4 which project out of half shells 12, 13. O-rings 21 are made of a hot water resistant plastic, preferably of heat- and chemical-resistant vulcanizable fluorelastomers based on vinylidene fluoride-hexafluoropropylene copolyermisates, sold commercially, for example, under the trademark VITON®.

Figure 9:
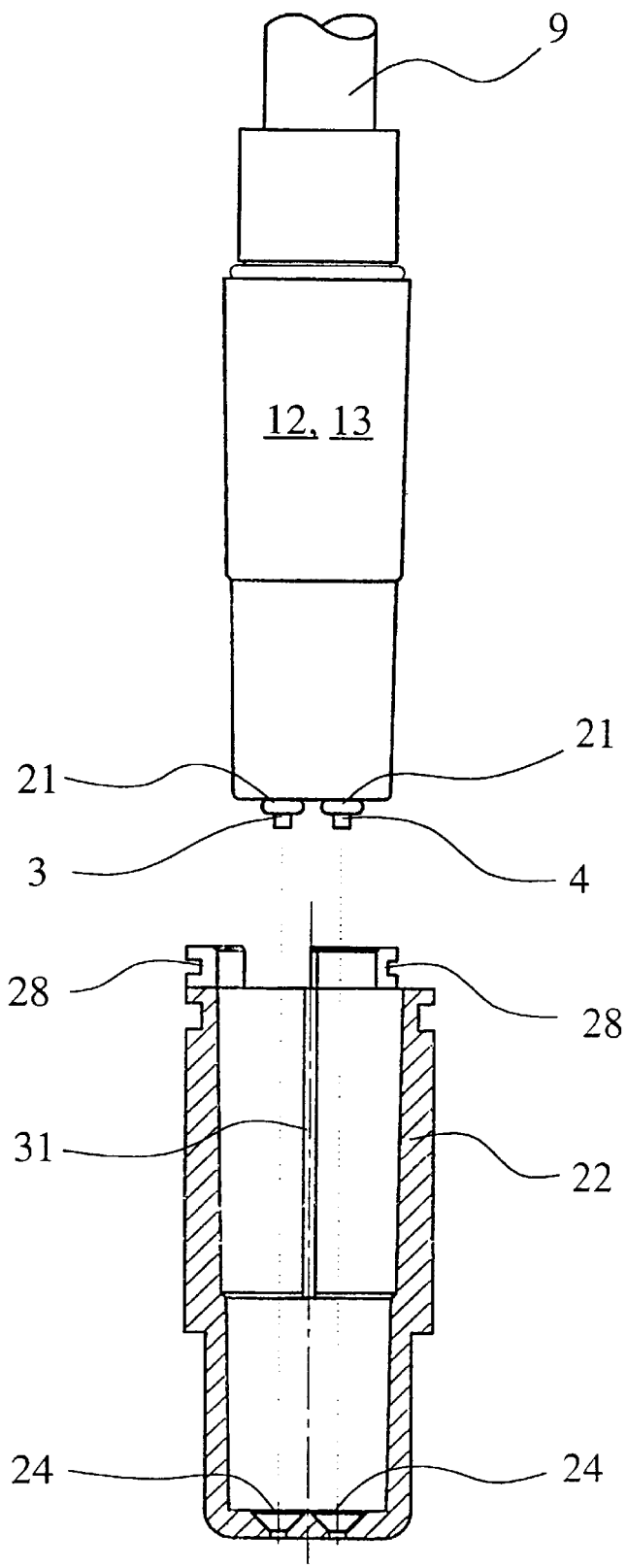
FIG. 9 shows the subject according to FIG. 8 and a cross section of one preferred embodiment of a lower housing sleeve of the heat transfer monitoring and/or measuring device according to the invention, prior to insertion of one into the other.
Figure 10:
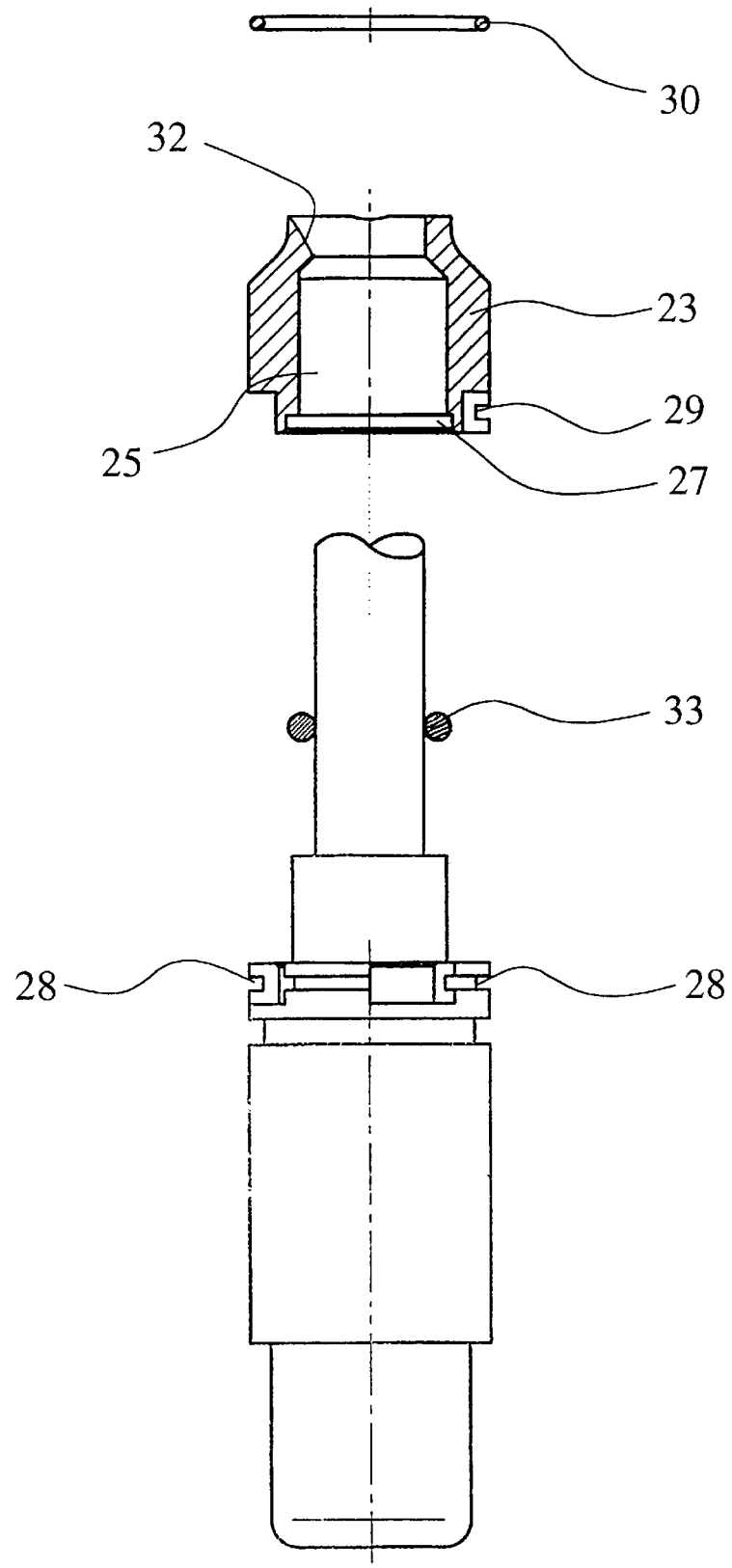
FIG. 10 is a view of the subject matter according to FIG. 9 in an assembled condition together with one preferred embodiment of an upper housing cover of the heat transfer monitoring and/or measuring device according to the invention, with the housing cover in cross section and prior to attachment thereof to the lower housing sleeve.

In the embodiment of a heat transfer indicating device according to the invention as is shown in FIGS. 9–11, another aspect of the invention is that housing 6 is formed of a lower housing sleeve 22 and an upper housing cover 23. Both the lower housing sleeve 22 and also the upper housing cover 23 are made of plastic, housing sleeve 22 preferably being made of polyester ether ketone (PEEK), and housing cover 23 preferably being made of polyphenylene sulfide (PPS).

As FIG. 9 shows, lower housing sleeve 22 of housing 6 has two recesses 24 which are assigned to heating element 3 and temperature measuring element 4. Recesses 24 partially hold the ends of heating element 3 and temperature measuring element 4 which project from half shells 12, 13 beyond the pushed-on O-rings 21.

Figure 12:
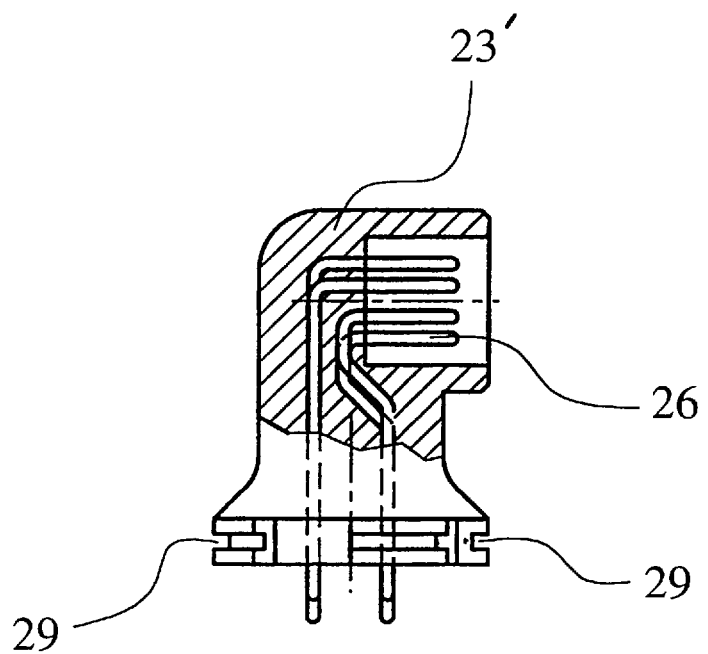
FIG. 12 is a partial cross-sectional view of another embodiment of an upper housing cover of the heat transfer monitoring and/or measuring device according to the invention.

As already stated, the embodiment of a heat transfer indicating device according to the invention shown in FIGS. 1 to 11 has a cable set 9 for electrical connection 5. Consequently, upper housing cover 23 is provided with a through-opening 25 for cable set 9. Conversely, FIG. 12 illustrates that electrical connection 5 can also be embodied as an attachment plug 26. Specifically, in FIG. 12 an upper housing cover 23' is shown which is provided with an attachment plug 26 that is integrated into housing cover 23.

As already noted, in the embodiment shown, half shells 12, 13 are provided with peripheral groove 18 and an O-ring 19 which is inserted into groove 18 to hold the half shells 12, 13 together. As apparent from FIG. 10, the upper housing cover 23 is bell-shaped and is provided with a peripheral groove 27 which is used to hold O-ring 19 in place.

FIGS. 9–11 also show that the lower housing sleeve 22 is provided with a groove 28 on its side facing upper housing cover 23 and the housing cover 23 is provided with a groove 29 on its side facing housing sleeve 22. The grooves 28, 29, which run over respective partial peripheral elements of the housing sleeve 22 and housing cover 23, become aligned to form a continuous annular groove when the facing sides of sleeve 22 and cover 23 are brought together. In this way, the lower housing sleeve 22 and upper housing cover 23 are able to be fixed and joined to one another by a spring washer 30 (which is shown separately in FIG. 10) being inserted into grooves 28, 29.

As briefly mentioned above, FIG. 7 illustrates that the joined half shells 12, 13 are externally provided with a guide crosspiece 20. Guide groove 31 (FIG. 9) provided in lower housing sleeve 22 corresponds to and receives this guide crosspiece 20.

Incidentally, it should be pointed out that, as apparent from FIG. 10, the through-opening 25 in upper housing cover 23 has a flared area 32, on its side that faces away from the lower housing sleeve 22, which increases in diameter in an outward direction away from sleeve 22. The radial orientation of flared area 32 corresponds to the radial alignment of heating element 3 and temperature measuring element 4.

In FIGS. 13–18, another embodiment of the invention is shown. In particular, in this embodiment, an outer housing 6' is comprised of a lower housing cover 34, a housing sleeve 35, and an upper housing cover 36. Both lower housing cover 34 and also upper housing cover 36 are made of plastic, while housing sleeve 35 is made of metal.

As FIGS. 13 and 14 show, heating element 3 and temperature measuring element 4 are pushed into lower housing cover 34 and are held using O-rings 37. In the front view of lower housing cover 34 according to FIG. 14, end surfaces 38 of heating element 3 and temperature measuring element 4 have large areas. Because the end surfaces 38 which are exposed to the medium flowing by the heat transfer indicating device are greatly enlarged, the temperature sensitivity of the heat transfer indicating device is improved.

Figure 16:
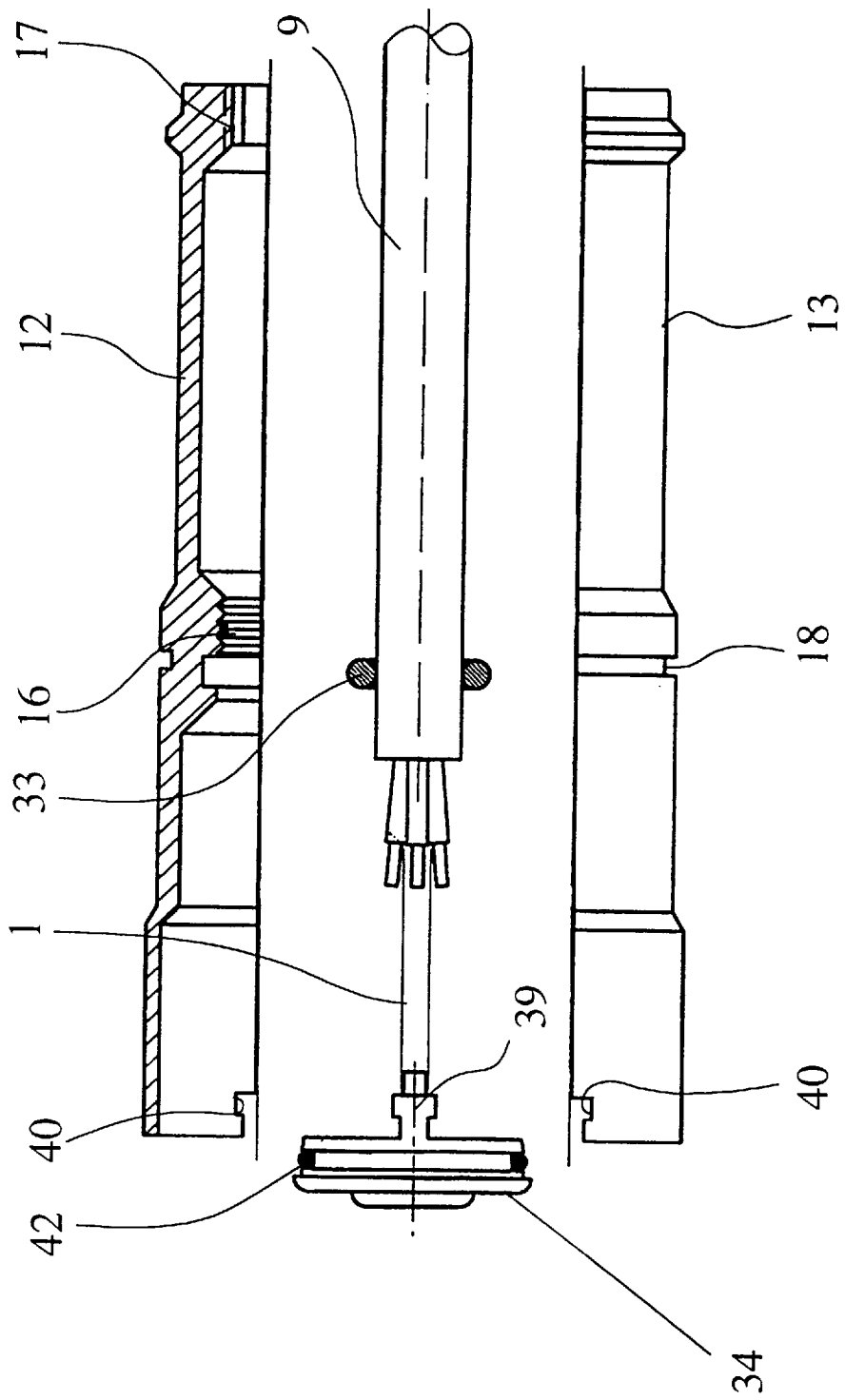
FIG. 16 shows the subject according to FIG. 15 together with two half shells in the unmounted state.

FIG. 15 shows component carrier 1, to one end of which the heating element 3 and temperature measuring element 4 are soldered and to the opposite end of which electrical leads 8 of cable set 9 are soldered. FIG. 16 shows two half shells 12 and 13 which have strain relief 16 and locking 17 for cable set 9. Lower housing cover 34 is held by a form fit mating of the knob-like projections 39 of lower housing cover 34 in recesses 40 of half shells 12 and 13.

FIG. 17 shows two mounted half shells 12 and 13 which are held together by an O-ring 19. Also an O-ring 42 is pushed into groove 41 of lower housing cover 34 shown in FIGS. 13 and 15. O-ring 42 seals the transition from lower housing cover 34 to housing sleeve 35 when housing sleeve 35 is pushed over the half shells 12 and 13. FIGS. 17 & 17A show an embodiment of the upper housing cover 36 from both the side and from the front. In the front view, a through-hole 25 through which cable set 9 can be routed can be seen.

FIG. 18 shows the completely assembled heat transfer indicating device with front housing cover 34, from which pin surfaces 38 of heating element 3 and temperature measuring element 4 project, housing sleeve 35 and upper housing cover 36, out of which cable set 9 is routed.

For mounting of the above described heat transfer indicating devices, the following applies:

For the first embodiment of FIGS. 1–12, initially, the component carrier 1 with electrical/electronic components 2 which are located thereon and connected to one another into a circuit, is in an unfolded condition. Heating element 3 and temperature measuring element 4 are placed on component carrier half 1b of the still unfolded component carrier 1 and are soldered to the assigned printed conductors. Then, the component carrier 1 is folded together so that component carrier halves 1a, 1b are located on top of one another and the heating element 3 and temperature measuring element 4 are located between the component carrier halves 1a, 1b, as shown in FIGS. 2 and 3. At this point, the electrical leads 8 of the cable set 9 are soldered to the electrical printed conductors which are provided on the external (viewed in the folded-together state) sides of component carrier halves 1a, 1b, but which are not shown in the figures. This results in the arrangement shown in FIG. 4.

The arrangement shown in FIG. 4 is then inserted into half shell 12 as shown in FIGS. 6 and 7. Afterwards, the half shell 13 is latched to half shell 12 using latching means 10, 11. In this state, fixing flanges 14 of heating element 3 and temperature measuring element 4 lie in recesses 15 of half shells 12, 13 and cable set 9 is relieved and secured against twisting by ribs 16, 17 of half shells 12, 13.

Next, the O-ring 19 is inserted into the peripheral groove 18 of half shells 12, 13, and the O-rings 21 are pushed onto the ends of heating element 3 and temperature measuring element 4 which project out of half shells 12, 13. This results in the arrangement shown in FIG. 8.

The arrangement shown in FIG. 8 is now inserted into lower housing sleeve 22 of housing 6, as FIGS. 9 and 10 show. The external guide crosspieces 20 provided on half shells 12, 13 and guide grooves 31 provided in housing sleeve 22 provide for correct alignment of the component shown in FIG. 8 with reference to lower housing sleeve 22, so that the ends of heating element 3 and temperature measuring element 4 which project out of half shells 12, 13 and pushed-on O-rings 21 are accommodated in recesses 24 in housing sleeve 22 provided for this purpose.

An O-ring 33, which comes to rest on the upper end of the half shells 12, 13, is now pushed over cable set 9. Afterwards, lower housing sleeve 22 and upper housing cover 23 are joined to one another, specifically by spring washer 30 coming to rest in grooves 28, 29 on housing sleeve 22 and housing cover 23.

Dimensioning is selected overall such that O-rings 21 pushed onto heating element 3 and temperature measuring element 4 and O-ring 33 seal housing 6 formed by lower housing sleeve 12 and upper housing cover 23.

Because the flared area 32 of cable through-hole 25 of upper housing cover 23 corresponds to the alignment of the heating element 3 and temperature measuring element 4, for example, the alignment of the heating element 3 and temperature measuring element 4 can be easily recognized even when the heat transfer indicating device is installed in a pipeline.

For the alternate embodiment of the heat transfer indicating device according to the invention, as is shown in FIGS. 13 through 18, first of all, the heating element 3 and temperature measuring element 4 are inserted with O-rings 37 into the openings of lower housing cover 34. Then, the heating element 3 and temperature measuring element 4, in the same way as electrical leads 8 of cable set 9, are soldered to electrical printed conductors on the still unfolded component carrier 1. Thus, lower housing cover 34 is also fixed securely relative to component carrier 1.

The arrangement shown in FIG. 15 is then, as shown in FIG. 16, inserted into one of the two half shells 12 or 13, which are then mounted to one another. When the shells are joined, the lower housing cover 34 is held by a form fit mating of the enlarged ends of knob-like projections 39 within recesses 40 of half shells 12, 13. O-ring 19 is inserted into peripheral groove 18 of the two half shells 12, 13 for additional fixing of the half shells 12, 13 to one another.

Then, the housing sleeve 35 is pushed over the half shells 12, 13 onto lower housing cover 34. The seal between housing sleeve 35 and lower housing cover 34 is accomplished by O-ring 42. The upper housing cover 36 is, then, pressed into the opening of housing sleeve 35 at its end that is opposite lower housing cover 34.

The important teachings of the invention are:
a) component carrier 1 is formed of two component carrier halves 1a, 1b located on top of one another, and the heating element 3 and temperature measuring element 4 are arranged between the component carrier halves 1a, 1b;
b) two half shells 12, 13 are provided to hold component carrier 1; and
c) a housing 6 is formed of lower housing sleeve 22 and upper housing cover 23, the lower housing sleeve 22 holding the assembled half shells 12, 13 with the component carrier 1 located between the half shells 12, 13; or a housing 6' is formed of lower housing cover 34, housing sleeve 35 and upper housing cover 36, the heating element 3 and temperature measuring element 4 being inserted with O-rings 37 through lower housing cover 34. These teachings lead to a heat transfer indicating device in which mounting is relatively simple, in which, consequently, use of casting resin can be abandoned and which can also be easily opened again, so that it can be repaired in case of a defect and parts not affected by the defect can be reused.

However, the important teachings of the invention can also be embodied and developed differently from the forms shown in the figures. In particular, housing 6 or lower housing sleeve 22 and upper housing cover 26 can have any shape and the connection of the lower housing sleeve 22 and upper housing cover 23 can also be accomplished in any other manner, for example, via a bayonet catch, a screw connection or by pinning, welding or pressing.

In the embodiments shown there are only a few electrical and/or electronic components 2 on component carrier 1. The embodiments of a heat transfer indicating device according to the invention shown are used in conjunction with an additional evaluation device. But, an embodiment is also possible in which an additional evaluation device can be omitted; therefore, all components required throughout are provided within housing 6 or 6'. For example, this can be done by upper housing cover 23 holding the components which otherwise would be provided in a separate evaluation device. Embodiments are also contemplated in which the electrical connection 5 provided in the illustrated embodiments is omitted, and instead, wireless signal transmission is implemented.

Therefore, while various embodiments in accordance with the present invention have been shown and described, it is understood that the invention is not limited thereto, and is susceptible to numerous changes and modifications as known to those skilled in the art. As such, this invention is not limited to the details shown and described herein, and includes all such changes and modifications as are encompassed by the scope of the appended claims.

I claim:

1. Heat transfer indicating device comprising a component carrier, a heating element, at least one temperature measuring element, an electrical power supply connection, a housing, and at least one of electrical and electronic components located on the component carrier and connected to one another to form a circuit; wherein the heating element and the at least one temperature measuring element are at least partially pin-shaped; and wherein the component carrier is formed of two component carrier halves located on top of one another with a portion of the heating element and the at least one temperature measuring element located between the component carrier halves; wherein two half shells are provided, and wherein the component carrier is fixed between the half shells wherein the heating element and the at least one temperature measuring element each have a peripheral fixing flange; and wherein the half shells have recesses which hold the fixing flanges of the heating element and at least one temperature measuring element.

2. Heat transfer indicating device comprising a component carrier, a heating element, at least one temperature measuring element, an electrical power supply connection, a housing, and at least one of electrical and electronic components located on the component carrier and connected to one another to form a circuit; wherein the heating element and the at least one temperature measuring element are at least partially pin-shaped; and wherein the component carrier is formed of two component carrier halves located on top of one another with a portion of the heating element and the at least one temperature measuring element located between the component carrier halves: wherein two half shells are provided, and wherein the component carrier is fixed between the half shells wherein an O-ring is on an end of each of the heating element and the at least one temperature measuring element which projects out of half shells.

3. Heat transfer indicating device according to claim 2, wherein the O-rings are made of a hot water-resistant plastic.

4. Heat transfer indicating device comprising a carrier, a heating element, at least one temperature measuring element, an electrical power supply connection, a housing, and at least one of electrical and electronic components located on the component carrier and connected to one another to form a circuit; wherein the heating element and the at least one temperature measuring element are at least partially pin-shaped; and wherein the component carrier is formed of two component carrier halves located on top of one another with a portion of the heating element and the at least one temperature measuring element located between the component carrier halves; wherein the housing comprises a lower housing sleeve and an upper housing cover; wherein the lower housing sleeve has two recesses, each of which receives a respective one of the heating element and the at least one temperature measuring element.

5. Heat transfer indicating device comprising a carrier, a heating element, at least one temperature measuring element, an electrical power supply connection, a housing, and at least one of electrical and electronic components located on the component carrier and connected to one another to form a circuit; wherein the heating element and the at least one temperature measuring element are at least partially pin-shaped; and wherein the component carrier is formed of two component carrier halves located on top of one another with a portion of the heating element and the at least one temperature measuring element located between the component carrier halves; wherein the housing comprises a lower housing sleeve and an upper housing cover; wherein two half shells are provided; wherein the component carrier is fixed between the half shells; wherein an O-ring encircles the half shells; and wherein the upper housing cover is provided with a peripheral groove which holds said O-ring.

6. Heat transfer indicating device comprising a carrier, a heating element, at least one temperature measuring element, an electrical power supply connection, a housing, and at least one of electrical and electronic components located on the component carrier and connected to one another to form a circuit; wherein the heating element and the at least one temperature measuring element are at least partially pin-shaped; and wherein the component carrier is formed of two component carrier halves located on top of one another with a portion of the heating element and the at least one temperature measuring element located between the component carrier halves; wherein the housing comprises a lower housing sleeve and an upper housing cover; wherein the lower housing sleeve on a side facing the upper housing cover and the upper housing cover on a side facing the lower housing sleeve are each provided with a groove which run over a respective partial peripheral element of the housing sleeve and the housing cover, the grooves of the partial peripheral elements being aligned to form a continuous annular groove; and wherein the lower housing sleeve and the upper housing cover are fixed and joined to one another by a spring washer in said annular groove.

7. Heat transfer indicating device comprising a carrier, a heating element, at least one temperature measuring element, an electrical power supply connection, a housing, and at least one of electrical and electronic components located on the component carrier and connected to one another to form a circuit; wherein the heating element and the at least one temperature measuring element are at least partially pin-shaped; and wherein the component carrier is formed of two component carrier halves located on top of one another with a portion of the heating element and the at least one temperature measuring element located between the component carrier halves; wherein the housing comprises a lower housing sleeve and an upper housing cover; wherein the electrical power supply connection comprises electrical leads of a cable set which are connected to the component carrier halves; and wherein the upper housing cover is provided with a through hole for the cable set; wherein an end of the cable through-hole in the upper housing cover that faces away from lower housing sleeve is provided with a flared area which increases in diameter in a direction away from the lower housing sleeve.

8. Heat transfer indicating device according to claim 7, wherein the flared area, the heating element and the at least one temperature measuring element are aligned with each other in a radial direction.

9. Heat transfer indicating device comprising a component carrier, a heating element, at least one temperature measuring element, an electrical power supply connection, a housing, and at least one of electrical and electronic components located on the component carrier and connected to one another to form a circuit; wherein the heating element and the at least one temperature measuring element are at least partially pin-shaped; and wherein the component carrier is formed of two component carrier halves located on top of one another with a portion of the heating element and the at least one temperature measuring element located between the component carrier halves; wherein the housing comprises a lower housing cover, a housing sleeve and an upper housing cover.

10. Heat transfer indicating device according to claim 9, wherein a respective O-ring is positioned on each of the heating element and the at least one temperature measuring element; and wherein portions of the heating element and the at least one temperature measuring element with the O-rings thereon extend into the lower housing cover.

11. Heat transfer indicating device according to claim 10, wherein the heating element and the at least one temperature measuring element are thermally conductive metal pins having externally exposed, diametrally enlarged surfaces portions.

12. Heat transfer indicating device according to claim 9, wherein the lower housing cover has knob-shaped projections thereon; wherein two half shells are provided which together define recesses of a shape which is matched to the knob-shaped projections of the lower housing cover; wherein the component carrier is fixed between the half shells; and wherein the lower housing cover is held in the half shells by a form fit between the knob-shaped projections of the lower housing cover and the recesses of the half shells.

13. Heat transfer indicating device according to claim 9, wherein the lower housing cover has a peripheral groove; and wherein an O-ring is disposed in said peripheral groove, said O-ring producing a seal between an inner surface of the housing sleeve and the lower housing cover.

14. Heat transfer indicating device according to claim 13, wherein the upper housing cover is made of an elastic material and pressed into the housing sleeve; wherein the electrical power supply connection comprises electrical leads of a cable set which are connected to the component carrier halves; and wherein the upper housing cover is provided with a through hole for the cable set.

15. Heat transfer indicating device according to claim 14, wherein the lower housing cover and the upper housing cover are made of plastic, and the housing sleeve is made of metal.

16. Heat transfer indicating device comprising a component carrier, a heating element, at least one temperature measuring element, an electrical power supply connection, a housing, and at least one of electrical and electronic components located on the component carrier and connected to one another to form a circuit; wherein the heating element and the at least one temperature measuring element are at least partially pin-shaped; wherein two half shells are provided; wherein the component carrier is fixed between the half shells; wherein the heating element and the at least one temperature measuring element each have a peripheral fixing flange; and wherein the half shells have recesses which hold the fixing flanges of the heating element and at least one temperature measuring element.

17. Heat transfer indicating device comprising a component carrier, a heating element, at least one temperature measuring element, an electrical power supply connection, a housing, and at least one of electrical and electronic components located on the component carrier and connected to one another to form a circuit; wherein the heating element and the at least one temperature measuring element are at least partially pin-shaped; wherein the housing comprises a lower housing cover, a housing sleeve and an upper housing cover; wherein a respective O-ring is positioned on each of the heating element and the at least one temperature measuring element; and wherein portions of the heating element and the at least one temperature measuring element with the O-rings thereon extend through the lower housing cover.

* * * * *